United States Patent [19]

Covey et al.

[11] 4,104,401

[45] Aug. 1, 1978

[54] CONTROL OF INSECTS AND ACARIDS WITH ALKYNYL PHENYLPHENOL DIVALENT ALIPHATIC SULFITES

[75] Inventors: Rupert A. Covey, Bethany; Robert E. Grahame, Jr., Cheshire, both of Conn.

[73] Assignee: Uniroyal, Inc., New York, N.Y.

[21] Appl. No.: 737,121

[22] Filed: Oct. 29, 1976

Related U.S. Application Data

[62] Division of Ser. No. 598,463, Jul. 23, 1975, Pat. No. 4,003,940, which is a division of Ser. No. 414,047, Nov. 8, 1973, Pat. No. 3,916,005.

[51] Int. Cl.² .................................................. A01N 9/14
[52] U.S. Cl. ................................................... 424/303
[58] Field of Search ................................ 424/335, 303

[56] References Cited

U.S. PATENT DOCUMENTS

| 3,179,682 | 4/1965 | Covey et al. ............ 260/456 |
| 3,272,854 | 9/1966 | Covey et al. ............ 260/456 |
| 3,428,734 | 2/1969 | Schmeling ............... 424/303 |

*Primary Examiner*—Albert T. Meyers
*Assistant Examiner*—D. W. Robinson
*Attorney, Agent, or Firm*—James J. Long

[57] ABSTRACT

Sulfites derived from alkynols and glycol ethers of phenylphenols are provided which are useful as insecticides and acaricides and which exhibit substantially reduced phytotoxicity than similarly used compounds. This invention also deals with the use of the novel sulfites in treating plants.

11 Claims, No Drawings

CONTROL OF INSECTS AND ACARIDS WITH ALKYNYL PHENYLPHENOL DIVALENT ALIPHATIC SULFITES

This is a division of application Ser. No. 598,463 filed July 23, 1975 (now U.S. Pat. No. 4,003,940, Jan. 18, 1977) which is in turn a division of Ser. No. 414,047 filed Nov. 8, 1973 (now U.S. Pat. No. 3,916,005, Oct. 28, 1975).

This invention relates to novel sulfite compounds which exhibit substantially reduced phytotoxicity levels and their use as insecticides and acaricides in treating plants.

BACKGROUND OF THE INVENTION

The prior art contains disclosures of sulfite comounds which have been effectively utilized as insecticides and acaricides and such compounds are particularly noteworthy with respect to the compounds of this invention in that the former do not contain an aromatic group which is substituted with an aryl group even though some of the prior art sulfite compounds have structures similar to those of this invention.

For example, U.S. Pat. No. 3,179,682 to Covey et al. discloses sulfite compounds of the formula:

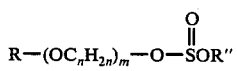

wherein R is an aromatic radical, such as phenyl or naphthyl, or a phenyl or naphthyl radical having one or more substituents selected from the group consisting of an alkyl group having up to nine carbon atoms, cycloalkyl, haloalkyl, alkoxy, nitro and halo, and R' is an acyclic alkynyl radical; $n$ to 2 to 10; and $m$ is 1 to 10.

Similarly, U.S. Pat. No. 3,272,854 to Covey et al. discloses sulfite compounds of the structure:

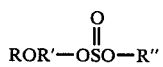

wherein R is as defined in the preceding paragraph or can be an aliphatic radical including cycloalkyl, alkoxy cycloalkyl, haloalkyl, cyanoalkyl and aryloxyalkyl, R' is a divalent cycloaliphatic radical in which the two valences are on two different carbon atoms, and R" is an aliphatic radical, including an alkynyl radical, or an aromatic radical. It is significant to note that, in each of the two, above-identified U.S. patents to Covey et al., R is not an aryl substituted aromatic group.

Other prior art patents related to this invention and having a glycol ether as one of the esterifying groups, but not an alkynyl group, are U.S. Pat. Nos. 2,529,494 and 2,320,808, both to Harris et al. Again, it is significant to note that the compounds disclosed in these patents do not contain an aryl substituted aromatic group.

THE INVENTION

It has been found that the novel alkynyl phenylphenol divalent aliphatic sulfites of this invention, which are particularly characterized by aryl substituted aromatic groups, exhibit a high activity enabling them to be effectively utilized as insecticides and acaricides. Significantly, it is the inclusion of aryl substituted aromatic groups in the compounds of the invention which readily distinguishes them from prior art compounds, such as those described above.

Surprisingly, the sulfite compounds of the invention also exhibit a significantly lower phytotoxic effect on plants which are treated with them than do prior art compounds employed in the same manner.

The alkynyl phenylphenoxyalkyl sulfites of the invention are represented by the general formula:

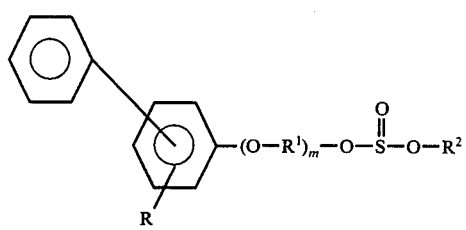

wherein R is hydrogen, bromine, chlorine, iodine or an alkyl radical having not more than 6 carbon atoms; $R^1$ is an alkylene radical containing from 2 to 6 carbon atoms or cycloalkylene radical containing 5 or 6 carbon atoms; $R^2$ is an alkynyl group containing from 3 to 6 carbon atoms; and, $m$ is an integer from 1 to 3.

Exemplary of the alkyl groups which R may represent are methyl, ethyl, n-propyl, isopropyl, n-butyl, 2-butyl, isobutyl, t-butyl, n-amyl, 2-amyl, t-amyl and hexyl.

Examples of $R^1$ are ethylene, 1,2 propylene, 1,2-butylene, 2,3-butylene, pentylene, hexylene, cyclopentylene, and cyclohexylene.

$R^2$ representatives are propargyl, 1-(2-butynyl), 1-(3-butynyl), 2-(3-butynyl), 1-(2-pentynyl), 2-(2-methyl-3-butynyl), 1-(2-hexynyl), and 1-(3-hexynyl).

In the preferred alkynyl phenylphenoxyalkyl sulfite compounds, the phenyl group is in the ortho position, R is hydrogen, $R^1$ is an alkylene radical containing 2-4 carbon atoms, $R^2$ is a propargyl or butynyl group, and $m$ is 1 or 2.

Generally, the alkynyl phenylphenoxyalkyl sulfites are prepared by reacting an alkynol with a chlorosulfinate of a glycol ether. The glycol ether is obtained by reacting a phenylphenol with an alkylene oxide or cycloalkylene oxide. The glycol ether is then reacted with thionyl chloride to produce the chlorosulfinate of glycol either and this chlorosulfinate is then reacted with an alkynol, as is illustrated by the following sequence:

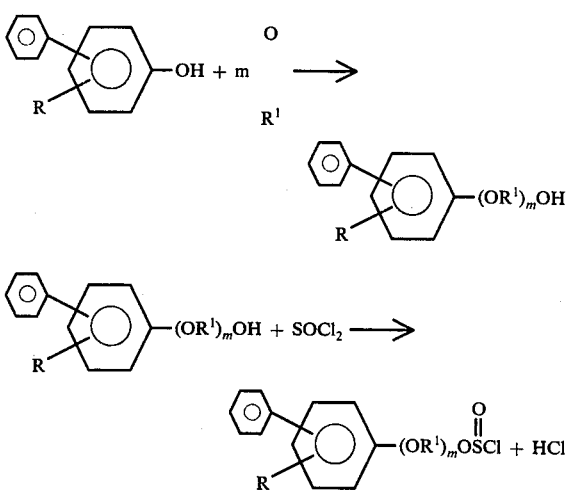

-continued

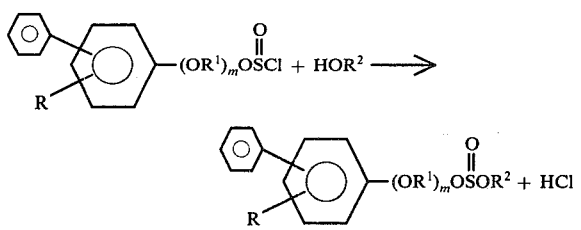

In general, the phenylphenol and sodium hydroxide, as catalyst (in amounts of about 1% based on the phenol), are combined and heated at temperatures from 160° to 190° C. prior to slowly adding the alkylene oxide reactant. The mixture is cooled and the catalyst is then neutralized with sulfuric acid. Upon heating under vacuum, the volatiles are removed and the glycol ether remains.

Glycol ethers prepared by this method assay about 95 to 98%. If further purification is desired, distillation or recrystallization may be employed, depending upon whether the glycol ethers are liquids or solids. When one equivalent of the alkylene oxide is used, the yield of the glycol ether is nearly quantitative. When more than one equivalent of the alkylene oxide reactant is used, mixtures of glycol ethers having one, two, or more units of oxide are obtained. These mixtures can be separated by means of distillation.

The chlorosulfinates are obtained by reacting the glycol ethers with excess thionyl chloride at ambient, or less than ambient, temperatures. For best yields, a standing or reaction time of 15 hours or more is required. Excess thionyl chloride is removed under reduced pressure and an approximately quantitative yield of the chlorosulfinate results. Assays of the chlorosulfinates will be about 95% or higher, but they are not purified at this point due to their instability. Instead, they are either reacted immediately with the alkynol or refrigerated and stored for later reaction with the alkynol.

Reaction of the chlorosulfinate with an alkynol is carried out at or below ambient temperature in an inert solvent, such as benzene or toluene, and in the presence of a hydrogen chloride acceptor, such as pyridine or dimethylaniline. The insoluble amine hydrochloride precipitates and is removed by washing with water. Any excess amine is removed by washing with dilute HCl. A dilute base wash is used to remove acidic impurities and the organic solution is brought to neutral using salt washes. The solvent is removed under vacuum and the product is filtered by using a filter-aid, such as Celite, a registered trademark product comprising a diatomaceous silica product. The final products are usually viscous oils which are difficult to purify because they are thermally unstable and cannot be distilled. Nevertheless, storage stability of these oils is fairly good in the presence of stabilizers such as propylene oxide.

Preparation of the novel sulfites of the invention and the effectiveness of their use as insecticides and acaricides will be better understood and become more clear from a consideration of the following Examples which are set forth as being illustrative of the invention and should not, in any way, be construed as being limitative thereof.

EXAMPLE 1

This Example describes the method of preparing propargyl 1-(o-phenylphenoxy)-2-butylsulfite.

o-Phenylphenol (34.0 g., 0.2 mole) and 0.3 g. of sodium hydroxide were combined and heated to 180° C. 1,2-Butylene oxide (15.8 g., 0.22 mole) was added dropwise over a 45 minute period while maintaining the reaction temperature at 180°–185° C. After the addition was completed, the mixture was stirred at this temperature for 30 minutes, cooled to 80° C., and neutralized with 0.2 ml. of concentrated sulfuric acid. The mixture was then heated at 65° C. (0.2 mm) in order to remove the water of neutralization and other volatiles. The yield of crude 1-(o-phenylphenoxy)-2-butyl glycol ether was 46.8 g. (97%). This compound can be used for preparing the chlorosulfinate without further purification.

The 1(o-phenylphenoxy)-2-butyl glycol ether was cooled to about 15°–20° C. and 18.2 ml. (29.8 g., 0.25 mole) of thionyl chloride was added over a 15 minute period while maintaining the temperature in this range. The mixture was then stirred for 15 minutes and allowed to stand at ambient temperature for 15 hours. Excess thionyl chloride and other volatiles were removed by warming the mixture to 30° C. (1.0 mm), whereupon 1-(o-phenylphenoxy)-2-butyl chlorosulfinate was obtained in nearly quantitative yield.

A solution of the 1-(o-phenylphenoxy)-2-butyl chlorosulfinate (32.4 g., 0.1 mole) in 50 ml. of benzene was cooled to 5° C. A solution of 5.9 g. (0.105 mole) of propargyl alcohol in 8.3 g. (0.105 mole) of pyridine was added dropwise over a 15 minute period while keeping the reaction temperature below 15° C. The mixture was then stirred for 20 minutes and washed with 50 ml. portions of water, 0.5N HCl, 0.5N NaOH and twice with a saturated NaCl solution. The solvent was removed under reduced pressure and the residue was warmed to 65° C. (0.3 mm) to remove the last traces of volatiles. The propargyl 1-(o-phenylphenoxy)-2-butyl sulfite was filtered through Celite filter aid. Product yield was 30.0 g. (87%)

Anal. Calculated for $C_{19}H_{20}O_4S$: S, 9.32 Found: S, 9.04.

EXAMPLE II

This Example describes the method of preparing propargyl o-phenylphenoxyethoxyethyl sulfite.

o-Phenylphenol (170 g., 1.0 mole) and 1.7 g. of sodium hydroxide pellets were combined and heated to 170° C. in a flask equipped with side-arm tube, thermometer and Dry Ice condenser. Ethylene oxide (b 88.0 g., 2 moles) was bubbled into the mixture below the surface of the liquid during 2.5 hours while keeping refluxing at a minimum and maintaining a reaction temperature of 170°–180° C. The mixture was then stirred for 15 minutes and cooled to 90° C. One milliliter of concentrated sulfuric acid was added to neutralize the sodium hydroxide. The fraction distilling between 172° and 186° C. (0.5 mm) was collected. The yield of o-phenylphenoxyethoxyethanol was 55.0 g. (21.3%). In addition to this product which contained two equivalents of ethylene oxide, compounds containing only one or three or more equivalents are also formed in considerable amounts.

The o-phenylphenoxyethoxyethyl chlorosulfinate was obtained by cooling a portion of the glycol ether prepared above (25.8 g., 0.1 mole) to 15° C. and then adding 9.4 ml. (15.4 g., 0.129 mole) thionyl chloride during 10 minutes while maintaining the reaction temperature between 10° and 15° C. The mixture was stirred for 30 minutes and then was allowed to stand at room temperature for 15 hours under a calcium chloride drying tube. Volatiles were removed by warming the mixture to 30° C. (1.0 mm). The chlorosulfinate was obtained in nearly quantitative yield.

A solution of 17.0 g. (0.05 mole) of the chlorosulfinate prepared above in 40 ml. benzene was cooled to 10° C. A solution of 3.3 g. (0.06 mole) propargyl alcohol in 4.8 ml. (4.7 g., 0.06 mole) pyridine was added dropwise during 15 minutes, the reaction temperature being maintained below 15° C. The mixture was stirred for 1 hour and was then washed with 50 ml. water, 50 ml. 0.5N HCl, 50 ml. 0.5N NaOH and twice washed with 50 ml. saturated NaCl solution. The solvent was removed under reduced pressure and the residue was warmed to 60° C. (0.5 mm) to remove volatiles. The product was filtered through Celite filter-aid and stabilized with 1% propylene oxide. Yield: 14.0 g. (78%).

Anal. Calculated for $C_{19}H_{20}O_5S$: S, 8.88. Found: S, 8.98. $n_D^{25}$ 1.5620.

While the methods in Examples I and II above describe a preferred manner for preparing the sulfites of the invention, it will be apparent to those skilled in the art that alternative methods may also be employed. For example, reacting the glycol ether with a separately prepared alkynyl chlorosulfinate, such as one prepared by reacting an alkynol with thionyl chloride, will also produce the sulfites of the invention.

Sulfur analyses of other sulfites made according to Examples I and II above are set forth in Table I below together with their refractive indexes ($n_D^{25}$) where determined:

TABLE I

| Sulfite | Sulfur Analysis Calc'd. | Sulfur Analysis Found | $n_D^{25}$ |
|---|---|---|---|
| Propargyl 2-(o-phenylphenoxy)-cyclohexyl sulfite | 8.66 | 7.93 | 1.5791 |
| Propargyl 1-(o-phenylphenoxy)-2-butyl sulfite | 9.32 | 9.04 | 1.5500 |
| Propargyl 1-(o-phenylphenoxy)-2-propyl sulfite | 9.72 | 9.29 | 1.5791 |
| Propargyl 2-phenylphenoxyethyl sulfite | 10.14 | 9.97 | 1.5825 |
| Propargyl 2-(p-phenylphenoxy)-cyclohexyl sulfite | 8.66 | 7.95 | |
| Propargyl 1-(p-phenylphenoxy)-2-butyl sulfite | 9.32 | 8.85 | 1.5750 |
| Propargyl 1-(4-chloro-2-phenylphenoxy)-2-propyl sulfite | 8.81 | 7.80 | 1.5738 |
| Propargyl 2-(2-chloro-4-phenylphenoxy)cyclohexyl sulfite | 7.92 | 7.07 | 1.5886 |
| Propargyl 4-t-butyl-2-phenylphenoxyethyl sulfite | 8.62 | 8.50 | 1.5631 |
| 1-(2-Butynyl) 2-(o-phenylphenoxy)-cyclohexyl sulfite | 8.35 | 8.55 | 1.5796 |
| 1-(2-Butynyl) 1-(o-phenylphenoxy)-2-butyl sulfite | 8.95 | 8.42 | 1.5651 |
| 1-(2-Butynyl) 1-(o-phenylphenoxy)-2-propyl sulfite | 9.32 | 8.73 | 1.5727 |
| 1-(2-Butynyl) 2-phenylphenoxyethyl sulfite | 9.72 | 9.57 | |
| 1-(2-Butynyl) 2-(p-phenylphenoxy) cyclohexyl sulfite | 8.35 | 7.63 | 1.5904 |
| 1-(2-Butynyl) 1-(p-phenylphenoxy)-2-butyl sulfite | 8.95 | 8.39 | 1.5730 |
| 1-(2-Butynyl) 1-(p-phenylphenoxy)-2-propyl sulfite | 9.32 | 9.11 | 1.5856 |
| 1-(2-Butynyl) 2-(4-chloro-2-phenylphenoxy) cyclohexyl sulfite | 7.65 | 6.70 | 1.5794 |
| 1-(2-Butynyl) 2-(2-chloro-4-phenylphenoxy)cyclohexyl sulfite | 7.65 | 6.86 | 1.5853 |
| 1-(2-Butynyl) 1-(2-chloro-4-phenylphenoxy)-2-propyl sulfite | 8.48 | 7.60 | 1.5853 |
| 1-(2-Butynyl) 4-t-butyl-2-phenylphenoxyethyl sulfite | 8.30 | 7.84 | 1.5643 |
| 1-(3-Hexynyl) o-phenylphenoxyethyl sulfite | 8.95 | 8.94 | 1.5631 |
| 1-(3-Butynyl) 2-phenylphenoxyethyl sulfite | 9.72 | 9.44 | 1.5845 |
| Propargyl m-phenylphenoxyethyl sulfite | 10.12 | 9.51 | 1.5956 |
| 1-(2-Butynyl) m-phenylphenoxyethyl sulfite | 9.69 | 9.64 | 1.5875 |
| 1-(2-Butynyl) o-phenylphenoxyethoxy ethyl sulfite | 8.55 | 8.12 | 1.5651 |
| Propargyl o-phenylphenoxyethoxyethyl sulfite | 8.88 | 8.98 | 1.5620 |

As mentioned earlier, the novel sulfites of the invention have been found to be useful for control of insects and acarids, including both mites and ticks, wherever they are found, such as on plants and animals or ponds, streams, rugs, walls, insulation, and the like.

These sulfites also surprisingly exhibit a significantly lower phytotoxicity on plants than similar, prior art compounds. As is known to the skilled artisan, these insecticides and acaricides can generally be formulated with a variety of suitable carrier mediums to provide compositions that can be applied in many different ways in the treatment of plants, it being understood that the term "plants" as used herein includes, without limitation, plant parts such as leaves and stems as well as seeds, fruits, vegetables, the soil in which they are grown, and the like.

One method of treatment utilizing the sulfites of the invention is through the use of a mixture of the sulfite compound with an inert medium, such as a dust of the sulfite compound admixed with or absorbed on naturally derived or synthetically obtained powdered, solid carriers such as mica, talc, diatomaceous earth, pyrophillite, clays, hydrated amorphous silica, and the like.

Another method entails employing the sulfite in admixture with powdered solid carriers and surfactants to form wettable powders, which may then be applied either directly or mixed with water to produce a suspension for application in that form.

Still a further method is through the use of an emulsion concentrate in a solvent system. The emulsion can be obtained by dissolving the sulfite compound in a suitable solvent such as acetone, benzene, xylene, toluene, hexane, kerosene, carbon tetrachloride, mesityl oxide or isophorone and admixing the solvated mixture with water containing a surface active dispersing agent. The surface active agents can be utilized in either emulsion concentrates or emulsifiable concentrates and can be nonionic, ionic, or cationic, which are inclusive of the well known dispersing agents such as are disclosed and described in U.S. Pat. No. 2,547,724.

Protection against insects and acarids can also be achieved by utilizing the sulfite in an aerosol spray. The sulfite can be dissolved directly in the aerosol propellent, which is a liquid under pressure but a gas at normal atmospheric pressure. Alternatively, the aerosol can be prepared by dissolving the sulfite in a less volatile solvent and then admixing the resultant solution with a highly volatile, liquid aerosol propellent.

Preferaby, the sulfites of the invention are applied by means of emulsifiable concentrates or wettable powders. Regardless of the manner of application, the amount of sulfite, as active ingredient (a.i.) can range between about 1.0 to 95% by weight. When application is by spraying, the amount of active sulfite can range from as little as about 1 part per million (ppm) to the undiluted concentrate which can then be applied by ultra low volume techniques. It should be clearly understood, however, that these ranges are merely illustrative since the particular concentration of the sulfite compound is not critical, but mainly a matter of convenience. For application to plant, it is important that about 0.1 to 10 pounds of active sulfite should be deposited per acre of planted area in order to obtain effective results. Usually, the particular amounts employed will depend upon such factors as the time of year, the size of the plants, the species and varieties of plants, the climatic conditions, and the like.

Accordingly, the following Examples are set forth to illustrate the efficacy of the sulfites of the invention when used as insecticides and acaricides.

EXAMPLE III

Mite Contact Test

This Example delineates the use of the sulfites of the invention at different concentrations in controlling mites.

Cotton, in the primary leaf stage and grown in 12 ounce cups under greenhouse conditions at 70°–75° F., was used. Two plants, which constituted four leaves, were tested at each chemical concentration. The upper surfaces of the untreated leaves were ringed with a one inch diameter circle of tanglefoot, a nontoxic adhesive preparation commonly used on flypapers and for ringing trees. The adhesive served to confine the mites to the upper leaf surfaces of the plant. Mites were transferred to the prepared leaves by placing sections of broad bean leaves heavily infested with two-spotted spider mites, *Tetranychus urticae* (L.), within the border of the adhesive preparation. Two-tenths gram of the sulfite chemical was mixed with one drop of polyoxyethylated vegetable oil dispersing agent dissolved in $2 \geqq 4$ ml. of acetone and brought to a total volume of 100 ml with distilled water. Dilutions of 500 ppm and 100 ppm were made from this solution using distilled water containing one drop of polyoxyethylated vegetable oil per 100 ml. distilled water.

The plants were sprayed with the dispersions of the sulfite chemicals at the different concentrations while the check plants were sprayed with aqueous solutions containing the dispersing agent and acetone without the sulfite chemicals. The spraying thoroughly wet the upper surface of the leaves, after which the plants were returned to the greenhouse to dry prior to conducting an initial count of the mites. The plants were kept in the greenhouse for five days whereupon a final count of the living mites remaining on the leaves was conducted. The percent control was ascertained from the following formula:

$$\text{Percent control } 100 \times \frac{\left( \frac{\% \text{ live mites on}}{\text{check plants}} - \frac{\% \text{ live mites on}}{\text{treated plants}} \right)}{\% \text{ live mites on check plants.}}$$

The percent mite control obtained with the sulfites of the invention is set forth in column A of Table II below, which also provides comparative results obtained with a commercial miticide comprising p-tert butylphenoxyisopropyl 2-chloroethyl sulfite as active ingredient and identified in Table II as "Standard."

TABLE II

| Sulfite | A Mite Contact Test % Control | | B Mosquito Larvae Test % Mortality | | C Phyto-toxicity rating |
|---|---|---|---|---|---|
| | 500 ppm | 100 ppm | 10 ppm | 1 ppm | |
| Propargyl 2-(o-phenylphenoxy) cyclohexyl sulfite | 100 | 100 | 100 | 50 | 1 |
| Propargyl 1-(o-phenylphenoxy)-2-butyl sulfite | 100 | 97 | 100 | 100 | 30 |
| Propargyl 1-(o-phenylphenoxy)-2-propyl sulfite | 100 | 100 | 100 | 100 | 25 |
| Propargyl 2-phenylphenoxyethyl sulfite | 100 | 100 | 100 | 100 | 24 |
| Propargyl 2-(p-phenylphenoxy) cyclohexyl sulfite | 91 | 79 | 100 | 45 | 0 |
| Propargyl 1-(p-phenylphenoxy)-2-butyl sulfite | 100 | 56 | 100 | 75 | 21 |
| Propargyl 1-(p-phenylphenoxy)-2-propyl sulfite | 100 | 62 | 100 | 80 | 25 |
| Propargyl 2-(4-chloro-2-phenylphenoxy)cyclohexyl sulfite | 100 | 69 | 95 | 40 | 5 |
| Propargyl 1-(4-chloro-2-phenylphenoxy)-2-propyl sulfite | 100 | 100 | 100 | 70 | 24 |
| Propargyl 2-(2-chloro-4-phenylphenoxy)cyclohexyl sulfite | 88 | 61 | 50 | 0 | 0 |
| Propargyl 1-(2-chloro-4-phenylphenoxy)-2-propyl sulfite | 100 | 69 | 100 | 100 | 2 |
| Propargyl 4-t-butyl-2-phenylphenoxyethyl sulfite | 100 | 95 | 85 | 20 | 0 |
| 1-(2-Butynyl)2-(o-phenylphenoxy)cyclohexyl sulfite | 100 | 81 | 80 | 0 | 0 |
| 1-(2-Butynyl) 1-(o-phenylphenoxy)-2-butyl sulfite | 100 | 92 | 100 | 100 | 0 |
| 1-(2-Butynyl) 1-(o-phenylphenoxy)-2-propyl sulfite | 100 | 100 | 95 | 15 | 1 |
| 1-(2-Butynyl) 2-phenylphenoxyethyl sulfite | 100 | 95 | 95 | 0 | 0 |
| 1-(2-Butynyl) 2-(p-phenylphenoxy)- | | | | | |

TABLE II-continued

| Sulfite | A Mite Contact Test % Control | | B Mosquito Larvae Test % Mortality | | C Phyto- toxicity rating |
| --- | --- | --- | --- | --- | --- |
| | 500 ppm | 100 ppm | 10 ppm | 1 ppm | |
| cyclohexyl sulfite | 100 | 46 | 90 | 0 | 0 |
| 1-(2-Butynyl) 1-(p-phenylphenoxy)-2-butyl sulfite | 98 | 19 | 100 | 100 | 2 |
| 1-(2-Butynyl) 1-(p-phenylphenoxy)-2-propyl sulfite | 100 | 44 | 100 | 8 | 6 |
| 1-(2-Butynyl) 2-(4-chloro-2-phenylphenoxy)cyclohexyl sulfite | 83 | 63 | 10 | 0 | 0 |
| 1-(2-Butynyl) 1-(4-chloro-2-phenylphenoxy)-2-propyl sulfite | 100 | 54 | 95 | 0 | 0 |
| 1-(2-Butynyl) 2-(2-chloro 4-phenylphenoxy)cyclohexyl sulfite | 56 | 34 | 0 | 0 | 0 |
| 1-(2-Butynyl) 1-(2-chloro-4-phenylphenoxy)-2-propyl sulfite | 94 | 35 | 100 | 100 | 0 |
| 1-(2-Butynyl) 4-t-butyl-2-phenylphenoxyethyl sulfite | 15 | 7 | 50 | 5 | 0 |
| 1-(3-Hexynyl) o-phenylphenoxyethyl sulfite | 18 | 15 | 100 | 50 | 0 |
| 1-(3-Butynyl) 2-phenylphenoxyethyl sulfite | 100 | 94 | 100 | 0 | 2 |
| Propargyl m-phenylphenoxyethyl sulfite | 98 | 91 | 100 | 100 | 11 |
| 1-(2-Butynyl) m-phenylphenoxyethyl sulfite | 98 | 71 | 100 | 80 | 45 |
| Propargyl o-phenylphenoxyethoxyethyl sulfite | 100 | 93 | 100 | 50 | 0 |
| 1-(2-Butynyl) o-phenylphenoxyethoxyethyl sulfite | 97 | 70 | 100 | 35 | 7 |
| Standard | 100 | 100 | 0 | 0 | 73 |

EXAMPLE IV

Mite 1 Day Residual Test

In this Example, the sulfites were utilized at different concentrations to determine acaricidal effectiveness.

The same type plants were used and the same procedure was followed as detailed in Example III except that the mites were transferred to the prepared leaves one day later. An initial mite count was then conducted. The plants were then kept in the greenhouse for five additional days, whereupon a final count of the living mites remaining on the leaves was made. The percent mite control was determined by employing the formula set forth in Example III above. The effectiveness of the sulfites in this test is shown in Table III below, which also shows a comparison of the sulfites with the same "Standard" identified and used in Example III above.

TABLE III

| Sulfite | Mite 1-day Residual Test % Control (ppm) | |
| --- | --- | --- |
| | 500 | 100 |
| Propargyl 2-(o-phenylphenoxy) cyclohexyl sulfite | 100 | 100 |
| Propargyl 1-(o-phenylphenoxy)-2-butyl sulfite | 100 | 100 |
| Propargyl 1-(o-phenylphenoxy)-2-propyl sulfite | 100 | 100 |
| Propargyl 2-phenylphenoxyethyl sulfite | — | 97 |
| 1-(2-Butynyl) 1-(o-phenylphenoxy)-cyclohexyl sulfite | 95 | 85 |
| 1-(2-Butynyl) 1-(o-phenylphenoxy)-2-butyl sulfite | 100 | 100 |
| 1-(2-Butynyl) 1-(o-phenylphenoxy)-2-propyl sulfite | 100 | 97 |
| 1-(2-Butynyl) 2-phenylphenoxyethyl sulfite | 100 | 100 |
| 1-(3-Butynyl) 2-phenylphenoxyethyl sulfite | — | 73 |
| Standard | 100 | 100 |

EXAMPLE V

Mosquito Larvae Control Test

This Example describes the use of the sulfites at different concentrations for controlling mosquito larvae.

Fourth instar larvae of *Aedes aegypti* (L.) mosquitos were used. After hatching, the larvae normally reach this stage of development in 5 days at 80° F.

One ml. of acetone and 100 ml. of water were added to 10 mg. of each sulfite to be tested to provide a concentration of 100 ppm. Dilutions of 10 and 1 ppm were made from this solution.

In duplicate, 25 ml. portions of each concentration of sulfite to be tested were placed in test tubes and from 5 to 25 mosquito larvae were added to each test tube. Checks without the sulfite chemical and plain water checks were also included. The tubes were held in darkness at 70° F. for 72 hours. Then, both live and dead larvae were counted to determine the percent mortality. The percent mortality of the larvae treated with the sulfites of the invention is shown in column B of Table II above.

EXAMPLE VI

Phytotoxicity Test

The low phytoxicity advantage of the sulfites of this invention is demonstrated by treating cowpeas with the sulfites according to the method described in this Example.

Cowpeas were grown in twelve-ounce cups under greenhouse conditions at 70°-75° F. for approximately 10 days. At this stage, two primary leaves are present and the new trifoliate growth is becoming evident (½ inch in length).

Eight-tenths gram of sulfite chemical was mixed with one drop of a polyoxyethylated vegetable oil dispersing agent dissolved in 2-4 ml. of acetone and brought to a total volume of 100 ml. with distilled water. Dilutions of 2000 ppm and 500 ppm were made from this solution using distilled water containing one drop of polyoxyethylated vegetable oil per 100 ml. distilled water.

The plants were sprayed with the dispersions of the sulfite chemicals at various concentrations and check plants were sprayed with aqueous solutions containing only the dispersion agent and acetone. The sprayings thoroughly wet the upper surfaces of the leaves, after which the plants were returned to the greenhouse and allowed to dry. Two cups, each containing two plants, were then treated at each chemical dosage. Five days later, phytotoxicity was determined at each dosage rate by calculating the percent damage to the leaves of each plant treated. The phytotoxicity determinations were made on both primary leaf tissue and trifoliate new growth. These determinations were then averaged to give a phytotoxicity rating. A phytotoxicity rating of "0" means no apparent phytotoxicity is present, while higher ratings relate to corresponding higher levels.

The phytotoxicity ratings determined according to this Example are set forth in Column C of Table II above.

While the invention has been described with particularity and in some detail, it is understood that many variations can be made therein without departing from the scope and spirit of the invention.

What is claimed is:

1. A method for killing insects and acarids, including mites and ticks, comprising applying to said insects or acarids or a locus subject to attack by said pests a pesticidally effective amount of a sulfite having the formula:

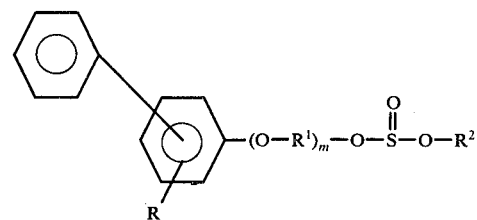

wherein R is hydrogen, bromine, chlorine, iodine or an alkyl radical having not more than 6 carbon atoms;
$R^1$ is an ethylene, 1,2-propylene, 1,2-butylene or 2,3-butylene radical or a cycloalkylene radical containing 5 or 6 carbon atoms;
$R^2$ is an alkynyl group containing from 3–6 carbon atoms; and, $m$ is an integer from 1 to 3.

2. The method of claim 1 wherein the phenyl group is in the ortho position; R is hydrogen; $R^2$ is a propargyl or butynyl group; and, $m$ is 1 or 2.

3. The method of claim 1 wherein said sulfite is propargyl 1-(o-phenylphenoxy)-2-butyl sulfite.

4. The method of claim 1 wherein said sulfite is propargyl 1-(o-phenylphenoxy)-2-propyl sulfite.

5. The method of claim 1 wherein said sulfite is propargyl 2-phenylphenoxy ethyl sulfite.

6. The method of claim 1 wherein said sulfite is 1-(2-butynyl) 1-(o-phenylphenoxy)-2-butyl sulfite.

7. The method of claim 1 wherein said sulfite is 1-(2-butynyl 1-(o-phenylphenoxy-2-propyl sulfite.

8. The method of claim 1 wherein said sulfite is 1-(2-butynyl) 2-phenylphenoxyethyl sulfite.

9. The method of claim 1 wherein said sulfite is 1-(3-butynyl) 2-phenylphenoxyethyl sulfite.

10. The method of claim 1 wherein said sulfite is propargyl 2-(o-phenylphenoxy) cyclohexyl sulfite.

11. The method of claim 1 wherein said sulfite is 1-(2-butynyl) 2-(o-phenylphenoxy)-cyclohexyl sulfite.